(12) United States Patent
Pitters

(10) Patent No.: US 12,226,237 B2
(45) Date of Patent: Feb. 18, 2025

(54) SYSTEM AND METHOD FOR HUMAN GAIT ANALYSIS

(71) Applicant: Lindera GMBH, Berlin (DE)

(72) Inventor: Helmut H. Pitters, Berlin (DE)

(73) Assignee: Lindera GmbH, Berlin (DE)

( * ) Notice: Subject to any disclaimer, the term of this patent is extended or adjusted under 35 U.S.C. 154(b) by 900 days.

(21) Appl. No.: 17/303,261

(22) Filed: May 25, 2021

(65) Prior Publication Data

US 2021/0275107 A1    Sep. 9, 2021

Related U.S. Application Data

(63) Continuation of application No. PCT/EP2019/077113, filed on Oct. 7, 2019.

(30) Foreign Application Priority Data

Nov. 26, 2018   (EP) .................................... 18208400

(51) Int. Cl.
*G06V 40/20* (2022.01)
*A61B 5/00* (2006.01)
(Continued)

(52) U.S. Cl.
CPC ............ *A61B 5/7275* (2013.01); *A61B 5/112* (2013.01); *A61B 5/1128* (2013.01);
(Continued)

(58) Field of Classification Search
CPC ....... G06V 40/25; A61B 5/112; A61B 5/1116; A61B 5/1123
See application file for complete search history.

(56) References Cited

U.S. PATENT DOCUMENTS

2017/0087416 A1*  3/2017  Hu ........................ G16H 20/30
2017/0231532 A1*  8/2017  Chakravarty ........ A61B 5/1122
                                                            600/595
2017/0243057 A1*  8/2017  Wu ......................... G06T 7/246

FOREIGN PATENT DOCUMENTS

WO           2017133009 A1     8/2017

OTHER PUBLICATIONS

X. Cai, G. Han, X. Song and J. Wang, "Single-Camera-Based Method for Step Length Symmetry Measurement in Unconstrained Elderly Home Monitoring," in IEEE Transactions on Biomedical Engineering, vol. 64, No. 11, pp. 2618-2627, Nov. 2017 (Year: 2017).*

(Continued)

*Primary Examiner* — Vu Le
*Assistant Examiner* — Jack Peter Kraynak
(74) *Attorney, Agent, or Firm* — Brake Hughes Bellermann LLP

(57) ABSTRACT

A computer-implemented method, computer program product and computer system for human gait analysis are described. A video stream of an individual walking includes a plurality of frames reflecting the walk of the individual. A skeletal motion of the individual is extracted, by inferring, from the obtained video stream, three-dimensional gait information. The three-dimensional gait information includes estimates of the individual's joint locations including at least the individual's foot locations on each frame, wherein the estimates are derived by matching for each frame two-dimensional coordinates of the respective frame with respective three-dimensional model information of the individual's body. One or more gait parameters of the individual may be determined, based on the individual's foot locations in local extrema frames showing local extrema of (Continued)

the distance between one foot location of the individual and a corresponding reference joint location.

17 Claims, 9 Drawing Sheets

(51) Int. Cl.
*A61B 5/11* (2006.01)
*G06N 3/08* (2023.01)
*G06T 7/246* (2017.01)
*G06V 10/75* (2022.01)
*G16H 50/20* (2018.01)
*G16H 50/30* (2018.01)
*G16H 50/50* (2018.01)
*G16H 50/70* (2018.01)

(52) U.S. Cl.
CPC ............. *A61B 5/7267* (2013.01); *G06N 3/08* (2013.01); *G06T 7/251* (2017.01); *G06V 10/75* (2022.01); *G06V 40/25* (2022.01); *G16H 50/20* (2018.01); *G16H 50/30* (2018.01); *G16H 50/50* (2018.01); *G16H 50/70* (2018.01); *G06T 2207/10016* (2013.01); *G06T 2207/20081* (2013.01); *G06T 2207/20084* (2013.01)

(56) References Cited

OTHER PUBLICATIONS

E. E. Stone and M. Skubic, "Passive in-home measurement of stride-to-stride gait variability comparing vision and Kinect sensing," 2011 Annual International Conference of the IEEE Engineering in Medicine and Biology Society, Boston, MA, USA, 2011, pp. 6491-6494 (Year: 2011).*
Chen, H. C., Ashton-Miller, J. A., Alexander, N. B., & Schultz, A. B. (1991). Stepping over obstacles: gait patterns of healthy young and old adults. Journal of gerontology, 46(6), M196-M203 (Year: 1991).*
BenAbdelkader, C., Cutler, R., Davis, L. (2002). View-invariant Estimation of Height and Stride for Gait Recognition. In: Tistarelli, M., Bigun, J., Jain, A.K. (eds) Biometric Authentication. BioAW 2002. Lecture Notes in Computer Science, vol. 2359. Springer, Berlin, Heidelberg (Year: 2002).*
J. Shotton et al., "Real-time human pose recognition in parts from single depth images," CVPR 2011, Colorado Springs, CO, USA, 2011, pp. 1297-1304 (Year: 2011).*
Dubois, A., & Charpillet, F. (2014). A gait analysis method based on a depth camera for fall prevention. Annual International Conference of the IEEE Engineering in Medicine and Biology Society. IEEE Engineering in Medicine and Biology Society. Annual International Conference, 2014, 4515-4518 (Year: 2014).*
X. Gu, F. Deligianni, B. Lo, W. Chen and G. Z. Yang, (2018), "Markerless gait analysis based on a single RGB camera," 2018 IEEE 15th International Conference on Wearable and Implantable Body Sensor Networks (BSN), Las Vegas, NV, USA, 2018, pp. 42-45 (Year: 2018).*
Dushyant Mehta, Srinath Sridhar, Oleksandr Sotnychenko, Helge Rhodin, Mohammad Shafiei, Hans-Peter Seidel, Weipeng Xu, Dan Casas, and Christian Theobalt. 2017. VNect: real-time 3D human pose estimation with a single RGB camera. ACM Trans. Graph. 36, 4, Article 44 (Aug. 2017) (Year: 2017).*
Shotton, J., Girshick, R., Fitzgibbon, A., Sharp, T., Cook, M., Finocchio, M., Moore, R., Kohli, P., Criminisi, A., Kipman, A., & Blake, A. (2013). Efficient human pose estimation from single depth images. IEEE transactions on pattern analysis and machine intelligence, (Year: 2013).*
Cheng et al.: "DenseCut: Densely Connected CRFs for Realtime GrabCut", Pacific Graphics, 2015, Vil. 34, No. 7, 9 pages.
F. Bogo et al.: "Keep it SMPL: Automatic Estimation of 3D Human Pose and Shape from a Single Image", obtainable at http://files.is.tue.mpg.de/black/papers/BogoECCV2016.pdf, Jul. 27, 2016, 18 pages.
He et al.: "Deep Residual Learning for Image Recognition", IEEE Conference on Computer Vision and Pattern Recognition, 2016.
International Search Report and Written Opinion for PCT Application No. PCT/EP2019/077113, mailed on Oct. 13, 2020, 15 pages.
Mehta, et al., "VNECT: Real-Time 3D Human Pose Estimation With a Single RGB Camera", arXIV.org, Cornell University Library, May 3, 2017, 13 pages.
Zhang, et al., "Dual Gait Generative Models for Human Motion Estimation From a Single Camera", IEEE Transactions on Systems, Man and Cybernetics, Part B: Cybernetics, IEEE Service Center, vol. 40, no. 4, Aug. 1, 2010, 15 pages.

\* cited by examiner

FIG. 4A

1200 computing step length gait parameter — 1210

FIG. 4B

1200 computing walking distance — 1220

↓ obtaining walking speed — 1230

FIG. 4C

1200 extrapolating walking floor plane — 1240

↓ determining local maximum frames indicative of maximum distances of foot locations from walking floor plane — 1250

↓ computing step height — 1260

FIG. 4D

1200 determining local minimum frames indicative of minimal distances between foot locations and reference location — 1270

↓ computing step height — 1280

SYSTEM AND METHOD FOR HUMAN GAIT ANALYSIS

CROSS REFERENCE TO RELATED APPLICATION

This application claims priority to, and is a continuation of, PCT/EP2019/077113, filed on Oct. 7, 2019 and entitled "SYSTEM AND METHOD FOR HUMAN GAIT ANALYSIS," which in turn claims priority to EP Application No. 18208400.4 filed on Nov. 26, 2018, both of which are hereby incorporated by reference in their entireties.

TECHNICAL FIELD

The present description generally relates to electronic data processing, and more particularly, relates to methods, computer program products and systems for human gait analysis usable for assessing the risk of fall (risk of falling accidents) of a human individual.

BACKGROUND

With growing age for many elderly people the risk of fall becomes an increasing threat to their health. Usually, medically trained persons try to assess this risk of fall for an individual patient from risk factors, such as for example, factors related to medication, psychological condition, and living environment of the patient. The Downton fall risk index, the STRATIFY fall risk assessment tool, and the Hendrich fall risk models I and II are well-known prior art tools for assessing the risk of fall. In such tools, firstly, a risk model contains a list of risk factors. For a particular patient one checks which of the risk factors apply. Finally, the overall risk score of the patient is a (weighted) sum of the risk factors present. If the risk score is larger than some cut-off value, the conclusion is that the corresponding patient has a high risk of falling.

In addition, sometimes the gait of patients is observed by the medically trained person and a subjective assessment of the gait is also taken into account when assessing the risk of fall. The various (weighted) factors are supposed to support the medically trained person to take appropriate measures for fall prevention. However, the subjective gait parameter observation may bear a risk that the observed gait parameters lack accuracy and may lead to wrong treatment actions.

There are tools available to determine gait parameters with high precision. Such tools are, for example, so-called gait carpets or systems based on multiple cameras. However, such tools typically require a technologically complex setup.

SUMMARY

There is therefore a need to provide systems and methods which allow a medically trained person to objectively assess the gait parameters of a patient, which are relevant for fall risk analysis, with equipment which requires a setup of lower complexity than the above mentioned tools.

To solve the above technical problem, computer-implemented method, computer system and computer program product are provided for human gait analysis in accordance with the independent claims.

In one example embodiment, a computer-implemented method is provided for human gait based on a video stream obtained from a monocular camera device. "Video stream" as used herein relates to a sequence of frames obtained by a video camera. Thereby, it is irrelevant whether the sequence of frames is directly processed in real time (stream processing) or whether the sequence of frames is stored in a storage device and processed off-line later on. The computer implemented method can be performed by a respective computer system which can execute a computer program implementing the modules which are configured to perform the respective method steps when being run on the computer system. Thereby, the monocular camera device can be any standard digital camera (e.g., a camera in a smartphone or tablet computer, a webcam, etc.). No particular technical requirements exist for the camera device which would go beyond the standard capabilities of such integrated camera devices. In particular, no stereo camera technology is required. The monocular camera device is used to obtain a video from a human individual (e.g., the patient) while the individual is walking. In other words, the obtained video stream includes a plurality of frames reflecting the walk of the human individual.

There are various methods available to the person skilled in the art to infer three-dimensional gait information, in particular the person's joint locations, from images or videos of a monocular camera. For example, estimated two-dimensional coordinates can be combined with location-maps derived (obtained) by using a convolutional neural network (referred to herein as the VNect approach). This example is explained in more detail below. In another implementation, three-dimensional surface models of a human body are used whose parameters are fitted to estimate two-dimensional coordinates.

In the following description, the VNect approach is described as an optional embodiment in more detail to illustrate how three-dimensional gait information can be extracted from the obtained video stream.

In a first step, a convolutional neural network (CNN) may be used to infer heat-maps and location-maps for joint location estimation of the individual's joints. This computation can be performed in real-time. The term "real-time" as used throughout this document is understood by a person skilled in the art of digital data processing as "near real-time" or "quasi real-time." Any digital data processing step (e.g., an image processing step) applied to data captured from the real world (e.g., sensor data to be transferred into visual representations of such sensor data) always results in a delay imposed by the digital data processing steps. For example, there is always a computational delay between the movement of the individual in the real world and the determination of the joint locations in a video frame. For convenience, only the term "real-time" will be used throughout this document when referring to such "near real-time" behavior of the disclosed methods and systems. The CNN is trained on three-dimensional human pose datasets. A particular heat-map describes, for a corresponding frame, probabilities that a particular joint of the individual is associated with respective pixels of the corresponding frame. Heat-maps are two-dimensional objects. A particular set of location-maps includes a plurality of location-maps, with each of the location maps describing the distance of a particular joint to a root location for the corresponding frame in a respective spatial dimension. That is, each location-map is a two-dimensional map for a corresponding spatial dimension. A particular set of location maps for three orthogonal spatial dimensions can be interpreted as a three-dimensional location map.

A CNN may be based on the ResNet50 network architecture. The layers of ResNet50 from res5a onwards are replaced with a VNECT architecture, producing the heat-maps and location-maps for all joints. After training, the Batch Normalization layers are merged with the weights of their preceding convolution layers to improve the speed of the forward pass. Two-dimensional heat-maps and three-dimensional location-maps are predicted from the features at res4d and res5a, tapering down the weights of intermediate losses with increasing iteration count. A person skilled in the art is also able to use other CNNs from the ResNet family as a basis for joint location estimation of the individual.

In VNect a default skeleton is used for kinematic skeleton fitting to finally capture the skeletal motion of the individual. However, using a default skeleton can lead to significant inaccuracies when trying to fit the default skeleton into video frames showing an individual whose skeleton shows significant deviations from the default skeleton. Therefore, before performing a kinematic skeleton fitting, the computer-implemented method described and/or claimed herein assesses a skeleton model for the individual which reflects the actual proportions of the individual.

This is achieved by firstly receiving a selection of at least a frame sequence of the video stream during which the joints of the individual move smoothly over time. For example, the selection may be received from the medically trained person based on this person's experience. Alternatively, image processing techniques can be used to automatically identify frame sequences where the movement of particular joints of the individual from one frame to the next frame stay within a predefined limit characteristic of a smooth movement. In example implementations, frame sequences which include the walking start of the person (i.e., typically the initial frame sequences) are less suited for assessing the individual's skeleton model.

The skeleton model of the individual is then estimated by determining, for each frame of the selected sequence, a loss for each joint of a default skeleton model in each spatial coordinate, and by adjusting the default skeleton model to compensate the determined losses to provide an adjusted skeleton model. In other words, for each frame of the selected sequence, an error is measured which describes the deviation of the joint locations associated with the default skeleton model versus the joint locations determined by the CNN when trying to fit the default skeleton with the determined joint locations. The default skeleton is then compensated by the measured errors over the entire selected frame sequence which results in the adjusted skeleton model reflecting the real proportions of the individual.

The following kinematic skeleton fitting is then performed using the adjusted skeleton model to determine a plurality of joint locations including at least the foot locations of the individual's feet on each frame. By using the adjusted skeleton model, accuracy with regards to the determination of the joint locations is improved.

Based on the individual's foot locations the system then determines one or more gait parameters of the individual which serve as an input for fall risk assessment. For this purpose, the computer system identifies local extrema frames showing local extrema of the distance between one foot location of the individual and a corresponding reference joint location. When the individual is smoothly walking, the distance of a foot of the individual to a reference joint location changes periodically showing local maxima and local minima between two consecutive touch points of the respective feet with the ground. In general, a reference joint location is the location of a further joint of the individual which provides a reference location inside the individual's body with respect to the foot location.

For example, if the reference location is the second foot of the individual, a local maximum of the distance is reached each time when the feet of the individual have reached the step length. The local minimum is reached at the moment the second foot passes the location of the first foot. When using as a reference point the point on the walking floor which has the shortest distance to a respective foot location this distance also changes periodically when walking smoothly in that the distance is zero when the respective foot touches the walking floor and reaches a local maximum between two consecutive touch point locations of the same foot.

In a real world scenario it may occur that multiple frames associated with a frame sequence where both feet of the individual are touching the ground show multiple local minima of this distance. In this case, the system may determine a cluster of honest local extrema frames (honest maximum frames and/or honest minimum frames) where the frames of the cluster contribute to the computation of the step length in that an average distance value is computed based on all frames of the respective cluster. In other words, honest local extrema frames include such frames which collectively reflect the distance between the individual's feet for a particular step of the individual. The average step length can then be determined by averaging the respective values for a plurality of honest local extrema (e.g., honest local maxima clusters).

It may occur that for a particular heat-map multiple pixels are associated with the same maximum probability value for the location of the respective joint. In such cases, the optimal pixel to be used for estimating the joint location with the following embodiment. In the predicting step the computer system first identifies a plurality of heat-map pixels in the particular heat-map wherein each of the identified pixels is associated with the same maximum probability value for the respective joint associated with the particular heat-map. Then, for each identified pixel, heat-map values in a predefined area adjacent to the identified pixel are integrated. For example, the adjacent area can be defined by a circle with the respective pixel at its center. The system thereby computes the integral of all probability values within the adjacent area. Finally, the system selects the identified pixel with the highest integral value as the pixel associated with the respective joint location. In this embodiment, the likelihood is increased to select the frame pixel which corresponds to the real world location of the particular joint. As a result, the accuracy of the predicting step is improved.

In some embodiments estimates of two-dimensional joint coordinates may be used as input which may be obtained, e.g. using approaches such as VNect, or DeepCut, or a convolutional pose machine, or any other method providing two-dimensional joint coordinates for that purpose. The SMPLify implementation referenced above may then be used to fit a three-dimensional human body model, e.g., the Skinned Multi-Person Linear Model (SMPL), to the two-dimensional joints. This model can be robustly fit to very little data. Moreover, the three-dimensional model prevents three-dimensional poses that may fit the two-dimensional joints, but cause interpenetration.

In a plurality of medical studies, three gait parameters have been identified as highly beneficial for assessing the risk of fall of a patient: the step length, the walking speed and the step height of the patient. Various implementations of "determining one or more gait parameters" allow to compute each of such parameters to be provided to the medically trained person.

In one example implementation, the step length gait parameter is computed by using the individual's (patient's)

second foot in a respective local maximum frame as the corresponding reference location. The system then computes the step length gait parameter as the mean value (e.g., average or median) of the distances between the individual's foot locations in the determined local maximum frames. For example, the distance between the individual's foot locations may be measured directly in a respective frame based on the corresponding three-dimensional coordinates. This measurement is advantageous when the patient's walk is passing by the camera and the frame pictures show a view of the patient from the side. The distance of any joint from the camera can be determined, for example, by using the pinhole projection model known by a person skilled in the art.

With a similar implementation the computer system may determine the walking speed gait parameter. In this implementation, the walking distance of the individual is computed based on the determined step length and the number of the local maximum frames identified in the video stream. The walking distance is then divided by the time interval associated with the sequence of frames associated with the walking distance to obtain the walking speed. Further implementations for determining the walking distance are disclosed in the detailed description.

In one implementation, the step height gait parameter is computed by using the location of the head (or pelvis) of the adjusted skeleton model as the corresponding reference location. In this implementation, the system identifies respective local minimum frames where a first distance between the foot location and the location of the reference point is shortest. In the same local minimum frames a second distance between the reference point and the second foot of the individual (the one touching the ground) can be computed. The step height can then be computed as a mean value of the difference between the first and second distances in the respective local minimum frames. Alternatively, the system may directly compute the distance between the individual's feet in local minimum frames.

In an alternative implementation, the system can determine the step height gait parameter by extrapolating a walking floor plane from floor contact points of the individual's feet. Such floor contact points can be derived from the local maximum frames used for determining the step length. Typically, when the patient walks smoothly, both feet touch the ground at the moment when there is a local maximum in the distance between the two feet. This is especially true for elderly people. Based on multiple contact points during the patient's walk, the walking floor plane can be extrapolated. Once the walking floor plane is known, the system can determine further local maximum frames with further local maxima of the distances of the individual's foot locations from the walking floor plane. Thereby, the shortest distance between a foot location and the floor plane is meant. The system then computes a mean value of the further local maximum distances as the step height.

In one embodiment, the previously determined gait parameters can be associated with respective scores characterizing a risk of fall for the individual. It may be advantageous to define scores which can easily be integrated into the prior art scoring systems for fall risk assessment as used in the healthcare industry. The determined gait parameter scores can then be provided as a result of the gait analysis to the medically trained person to support the decision making for an effective treatment of the patient to reduce the risk of fall for the patient.

In one embodiment, a computer program product is provided including instructions that, when loaded into a memory of a computing device and executed by at least one processor of the computing device, execute method steps of computer implemented methods as disclosed herein.

In one embodiment, a computer system for human gait analysis is provided. The computer system is configured to run the computer program product which allows to execute the steps of the disclosed computer-implemented method. For this purpose, the computer system implements the following modules via the computer program product to perform the respective gait analysis functions: an interface configured to obtain a video stream from a monocular camera device, the video stream comprising a plurality of frames reflecting the walk of a human individual; a skeletal motion extractor configured to extract from the video stream a skeletal motion associated with the individual by inferring, from the obtained video stream, three-dimensional gait information wherein the three-dimensional gait information includes estimates of the individual's joint locations including at least the individual's foot locations on each frame, the estimates being derived by matching for each frame two-dimensional coordinates of the respective frame with respective three-dimensional model information of the individual's body; and a gait parameter determining module configured to determine one or more gait parameters of the individual based on the individual's foot locations in local extrema frames showing local extrema of the distance between one foot location of the individual and a corresponding reference location.

In an optional embodiment, the extractor module further comprises a prediction module using a convolutional neural network, trained on three-dimensional human pose datasets, configured to predict heat-maps and location-maps for joint location estimation in real-time, wherein a particular heat-map describes, for a corresponding frame, probabilities that a particular joint is associated with respective pixels of the corresponding frame, and wherein a particular set of location-maps includes a plurality of location-maps, with each of the location maps describing the distance of a particular joint to a root location for the corresponding frame in a respective spatial dimension; a skeleton model estimator module configured to select at least a frame sequence of the video stream during which the joints of the individual move smoothly over time, and configured to estimate a skeleton model of the individual by determining, for each frame of the selected sequence, a loss for each joint of a default skeleton model in each spatial coordinate, and configured to adjusting the default skeleton model to compensate the determined losses to provide an adjusted skeleton model; and a skeleton fitting module configured to perform kinematic skeleton fitting per video frame using the adjusted skeleton model to determine a plurality of joint locations including at least the foot locations of the individual's feet on each frame.

In one embodiment, the prediction module is further configured to identify a plurality of heat-map pixels in a particular heat-map wherein each of the identified pixels is associated with the same maximum probability value for the respective joint associated with the particular heat-map; for each identified pixel, integrate heat-map values in a predefined area adjacent to the identified pixel; and select the identified pixel with the highest integral value as the pixel associated with the respective joint location.

In a further example embodiment, the extractor module further comprises a two-dimensional joint coordinate estimator module configured to provide, for each frame, estimates of two-dimensional joint coordinates of each joint, together with a confidence value for each joint; and a three-dimensional fitting module configured to fit a three-dimensional human body model to the two-dimensional joint coordinates.

In further embodiments of the computer system, the gait parameter determining module implements the various gait parameter determination methods as disclosed herein.

Further aspects will be realized and attained by means of the elements and combinations particularly depicted in the appended claims. It is to be understood that both the foregoing general description and the following detailed description are exemplary and explanatory only, and are not restrictive of the invention as described.

BRIEF DESCRIPTION OF THE DRAWINGS

FIGS. 4A to 4D illustrate various options for determining various gait parameters from the video stream.

DETAILED DESCRIPTION

Figure 1:
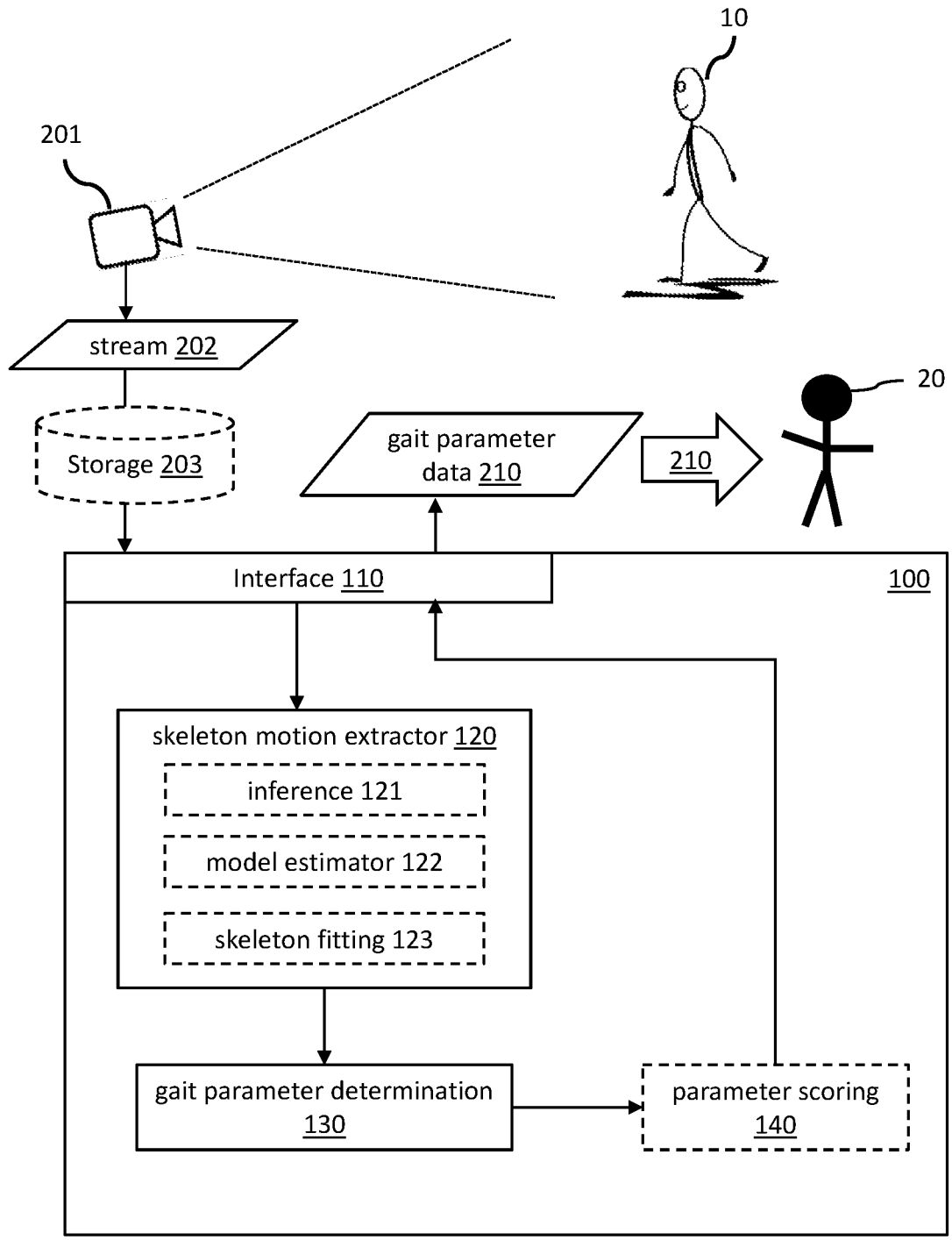
FIG. 1 includes a simplified block diagram of a computer system for human gait analysis based on a video stream obtained from a monocular camera device according to an embodiment.

FIG. 1 includes a simplified block diagram of a computer system 100 for human gait analysis based on a video stream 202 obtained from a monocular camera device 201 according to an embodiment. FIG. 1 will be described in the context of the flow charts of FIGS. 2A, 2B, 3, and 4A-4D showing simplified flow charts of a computer-implemented method for human gait analysis according to various embodiments. For this reason, the following description includes reference numbers from all of such figures.

The computer system 100 includes an interface 110 configured to obtain the video stream 202 which is provided by the monocular camera device 201. The video stream can be obtained directly from the camera 201 wherein real-time analysis of the individual's gait parameters is intended based on a live stream. It may also be obtained from a video storage 203 to perform offline analysis of previously recorded videos. The video stream 202 includes a plurality of frames reflecting the walk of a human individual 10. In other words, the camera 201 is positioned such that the walk of the individual occurs within the viewing angle of the camera indicated by the dotted lines. The interface 110 is configured to receive the frames of the video stream in the format in which they are recorded or preprocessed by the camera device 201, or in the format they are stored in the video storage 203. The video storage can be any data storage configured to store the sequence of video frames of stream 202. For example, the storage 203 can be on a remote storage device (e.g., on a so-called cloud server) or it can be an integral component of the system 100.

The system 100 further includes a skeletal motion extractor 120 which is configured to extract, from the video stream 202, a skeletal motion associated with the individual 10. For the purpose of skeletal motion extraction the extractor infers 1100 three-dimensional gait information from the obtained video stream. The three-dimensional gait information includes estimates of the individual's joint locations including at least the individual's foot locations on each frame. The estimates are derived by matching for each frame two-dimensional coordinates of the respective frame with respective three-dimensional model information of the individual's body. Various extraction approaches can be applied by the person skilled in the art. In one estimated two-dimensional coordinates can be combined together with location-maps derived by using a convolutional neural network (VNect approach). In the VNect approach, advantageously, the camera 201 is a monocular RGB camera device. In another implementation, three-dimensional surface models of a human body are used whose parameters are fitted to estimated two-dimensional coordinates (SMPLify approach).

In the example improved VNect implementation (dashed boxes), an inference module 121 of the extractor 120 uses a convolutional neural network CNN, trained on three-dimensional human pose datasets. The CNN is configured to derive 1110 heat-maps and location-maps for joint location estimation. This can be performed in real-time in scenarios where gait analysis if performed on the basis of a live video stream. Thereby, a particular heat-map describes, for a corresponding frame, probabilities that a particular joint is associated with respective pixels of the corresponding frame. A particular set of location-maps (3D location map) includes a plurality of location-maps, with each of the location maps describing the distance of a particular joint to a root location for the corresponding frame in a respective spatial dimension. The set includes location maps in three spatial dimensions thus representing a 3D location map.

A skeleton model estimator module 122 of the extractor 120 can be used to improve the VNect-based implementation to achieve a higher degree of accuracy for the derived joint locations of the individual. In existing approaches, the following kinematic skeleton fitting is directly applied by using a default skeleton model for all individuals. This may lead to large errors (loss) in cases where the individual's real skeleton dimensions show substantial deviations from the dimensions of the default skeleton model. To overcome this drawback, it is suggested to firstly estimate a skeleton model of the individual which comes close to the real skeleton of the individual, and, later on, perform kinematic skeleton fitting based on the estimated skeleton model. Thereby, the respective loss is reduced substantially and higher accuracy is achieved for the determination of the individual's joint locations.

The model estimator 122 firstly selects at least a frame sequence of the video during which the joints of the individual move smoothly over time. A smooth movement in this sense is a movement which lacks any discontinuities in the sense that the joints of the individual do not move over substantial distances from one frame to the next frame. A substantial distance corresponds to a distance where the movement of a body part of the individual results in a change of pixel coordinates in subsequent frames indicating an abrupt or erratic movement for this body part. Examples of discontinuous movements occur when the individual is running or jumping, or when the individual is beginning to move from a prior standing or sitting position. The model estimator may receive 1120 indicators from an operator 20 (e.g. a medically trained person) of the system 100 which indicate a start and a stop frame enclosing a frame sequence with smooth movement and the selects the corresponding frame sequence. In an alternative implementation, the model estimator may apply standard image processing techniques to identify such a smooth movement sequence in the video stream in accordance with predefined rules defining threshold values for joint movement over two or more frames which specify the beginning of discontinuous movements.

Then, the model estimator estimates 1130 a skeleton model of the individual by determining, for each frame of the selected sequence, a loss for each joint of a default skeleton model in each spatial coordinate, and by adjusting the default skeleton model to compensate the determined losses to provide an adjusted skeleton model. The adjusted skeleton model now reflects the real skeleton of the individual with a higher accuracy than the default skeleton model which was used as a starting point.

Finally, in the improved VNect implementation, a skeleton fitting module 123 of the extractor performs 1140 kinematic skeleton fitting per video frame using the adjusted skeleton model to determine a plurality of joint locations of the individual 10. It is to be noted that the determined joint locations also include the joints of the individual indicating the individual's foot locations on each frame. Kinematic skeleton fitting can be performed in accordance with the VNect method(s), with the default skeleton model in the VNect approach replaced by the estimated skeleton model.

Figure 3:
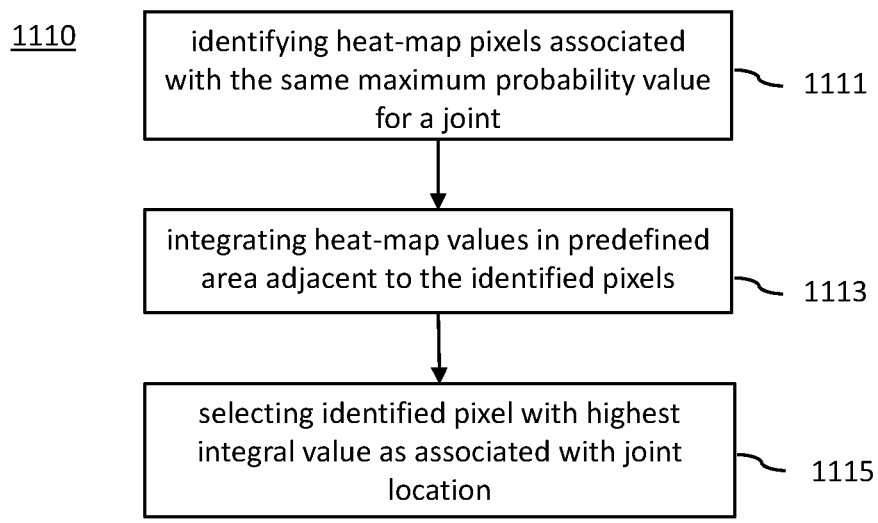
FIG. 3 illustrates an example computer-implemented method for improved joint location determination according to an embodiment.

A further improved embodiment of the VNect implementation is illustrated by the flow chart of FIG. 3. In this embodiment, the prediction module is further configured to identify 1111 a plurality of heat-map pixels in a particular heat-map wherein each of the identified pixels is associated with the same maximum probability value for the respective joint associated with the particular heat-map. For each identified pixel, an integral value is computed by integrating 1113 heat-map values in a predefined area adjacent to the identified pixel integrate. Then the identified pixel with the highest integral value is selected 1115 as the pixel associated with the respective joint location for the further processing.

Figure 5:
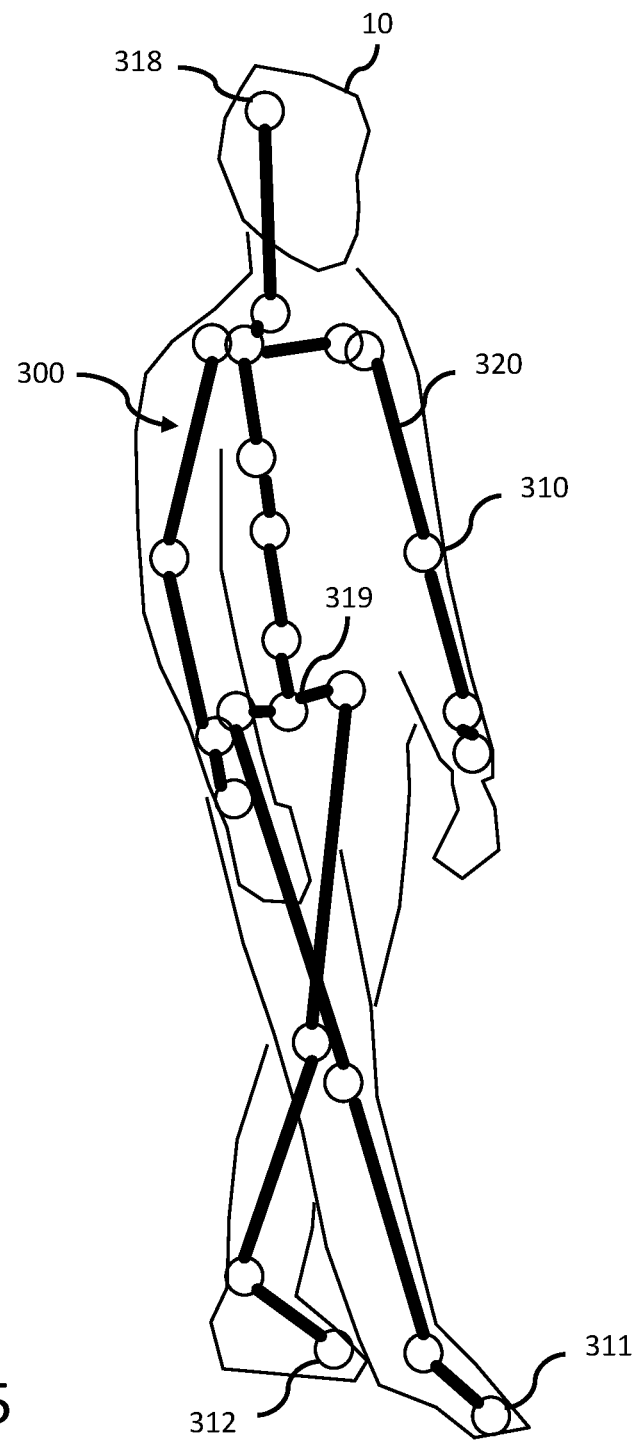
FIG. 5 shows an example of an adjusted skeleton model for a respective individual in a side view.
Figure 6:
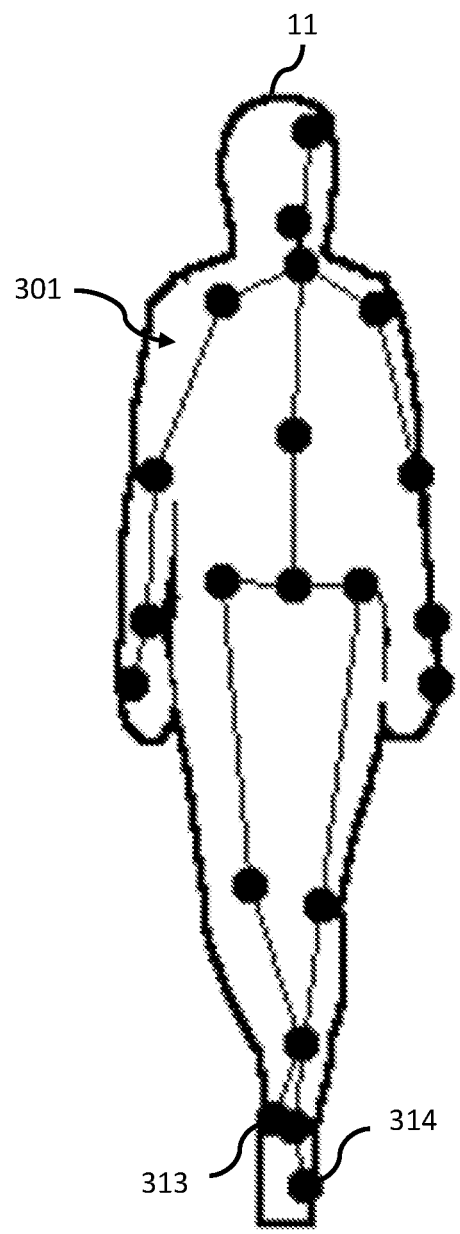
FIG. 6 shows example of an adjusted skeleton model for a respective individual in a front view.

Turning briefly to FIG. 5, the estimated skeleton model 300 of the individual 10 is illustrated for the individual 10 with a viewing angle from the side. In FIG. 5, the joint locations are illustrated by respective circles 310, 311, 312, and the connections between the joints (e.g., bones) are illustrated by bold lines 320. The determined foot locations may correspond to the joints 311 and 312. In FIG. 6, the estimated skeleton model 301 for an individual 11 is illustrated with a viewing angle from the front. In FIG. 6, the joint locations are illustrated by respective bullets 313, 314 connected again by straight lines. In the example of FIG. 6, the joints 313, 314 may correspond to the individual's foot locations.

Figure 2A:
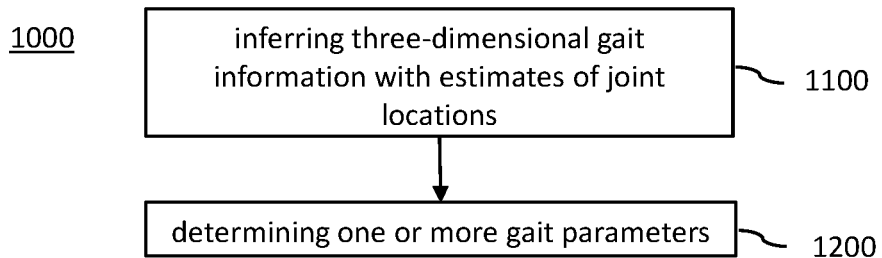
FIGS. 2A, 2B, 2C are simplified flow charts illustrating a computer-implemented method for human gait analysis according to various embodiments.
Figure 2B:
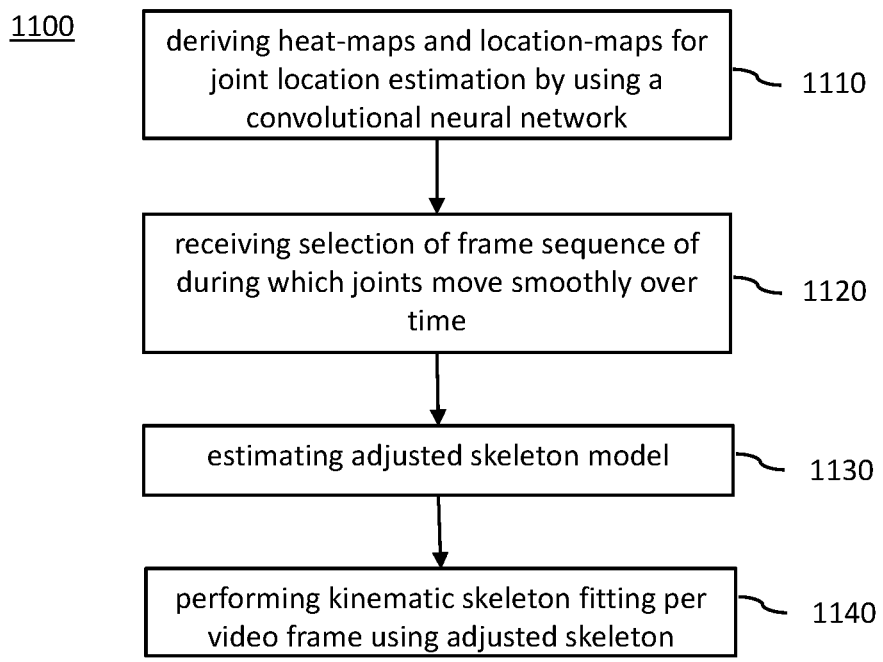
Figure 2C:
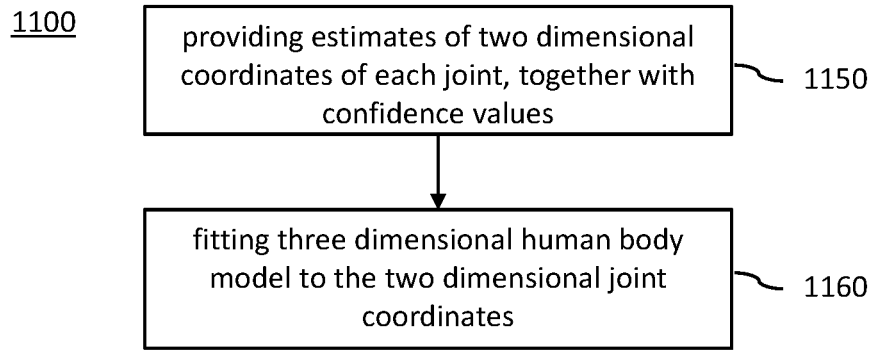

Now turning back to the general description of FIG. 1 in combination with FIG. 2C, in the alternative implementation based on the SMPlify approach, the extractor 120 works similar to the VNect implementation in that both implementations use estimates of two-dimensional coordinates of skeleton joints and infer three-dimensional information on the human pose via an optimization procedure based on the two-dimensional data of the joint coordinates. In addition to the three-dimensional human pose information, the SMPLify implementation also infers three-dimensional information regarding the individual's shape.

The SMPLify implementation allows for automatic estimation of three-dimensional pose and three-dimensional shape of a human body (e.g., the individual's body) from a single unconstrained image. As input SMPLify requires estimates of the two-dimensional coordinates of each joint, together with a confidence value for each joint. These two-dimensional estimates can, in principle, be provided 1150 by any appropriate method known by the skilled person. For example, CNN-based methods may be used, or a convolutional pose machine may be employed. SMPLify then fits 1160 a three-dimensional human body model, e.g., the Skinned Multi-Person Linear Model (SMPL), to the two-dimensional joints. This model can be robustly fit to very little data. Moreover, the three-dimensional model prevents three-dimensional poses that may fit the two-dimensional joints, but cause interpenetration.

The SMPLify implementation requires estimates of two-dimensional joint coordinates as input which may be obtained, e.g. from VNect, or DeepCut, or a convolutional pose machine, or any other method providing two-dimensional joint coordinates for that purpose. Compared to the VNect implementation, SMPlify does not rely on location maps but uses the SMPL three-dimensional body mode. In contrast to the VNect implementation the SMPLify solutions does not allow for interpenetration. This may be advantageous in many gait analysis scenarios. An advantage of the VNect implementation can be that VNect performs in real time.

The joint locations as determined by the extractor 120 are then used by a gait parameter determining module 130 of the system 100 to determine one or more gait parameters of the individual 10 based on the individual's foot locations in local extrema frames showing local extrema of the distance between one foot location of the individual and a corresponding reference location. In other words, the gait parameter determining module identifies frames in the video stream where a foot of the individual has a minimum or a maximum distance from a reference point when compared to the preceding frame and the subsequent frame. The type of reference point for a particular computation depends on the type of gait parameter to be determined.

The scenarios illustrated in FIGS. 4A to 4D illustrate computer-implemented method steps for determining gait length, gait speed and gait height parameters of the individual 10. Such parameters provide relevant information for a medically trained person to assess the risk of fall for the individual 10. Such figures are now discussed in more detail in the context of the scenarios illustrated in FIGS. 7 and 8.

Figure 7A:
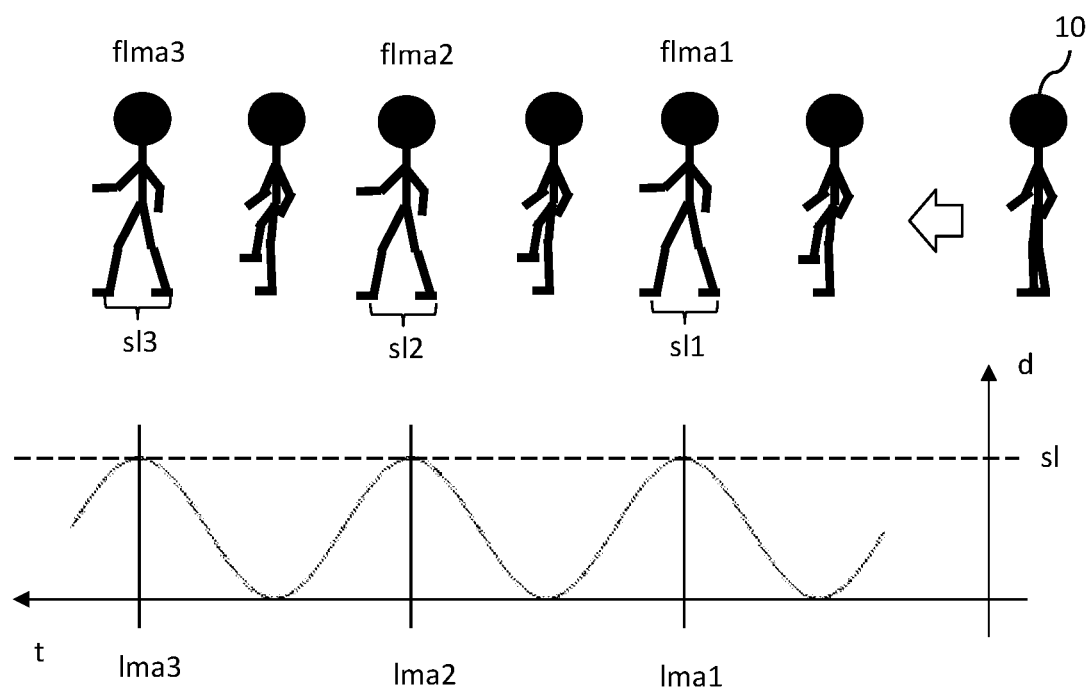
FIG. 7A illustrates step length gait parameter determination according to an embodiment.

In FIG. 4A, the step 1200 further includes computing step 1210 to determine a step length gait parameter. FIG. 7A illustrates that the corresponding reference location is the location of the individual's second foot in a respective local maximum frame flma*. The individual 10 starts walking at the right hand of FIG. 7A in the left direction. The video frames flma1, flma2 and flma3 always show the individual when the distance between the two feet of the individual reaches a local maximum sl1, sl2, sl3. The lower part of FIG. 7A illustrates schematically how the distance d between the two feet evolves over time t. The behavior is similar to a sine curve. The local minima are reached when during walking one foot passes the other foot. The local maxima lma1, lma2, lma3 are typically present when both feet are touching the ground. In other words, a local maximum frame occurs when the distance of one foot location to a respective reference joint location reaches a maximum value in comparison with previous and subsequent frames.

Figure 7B:
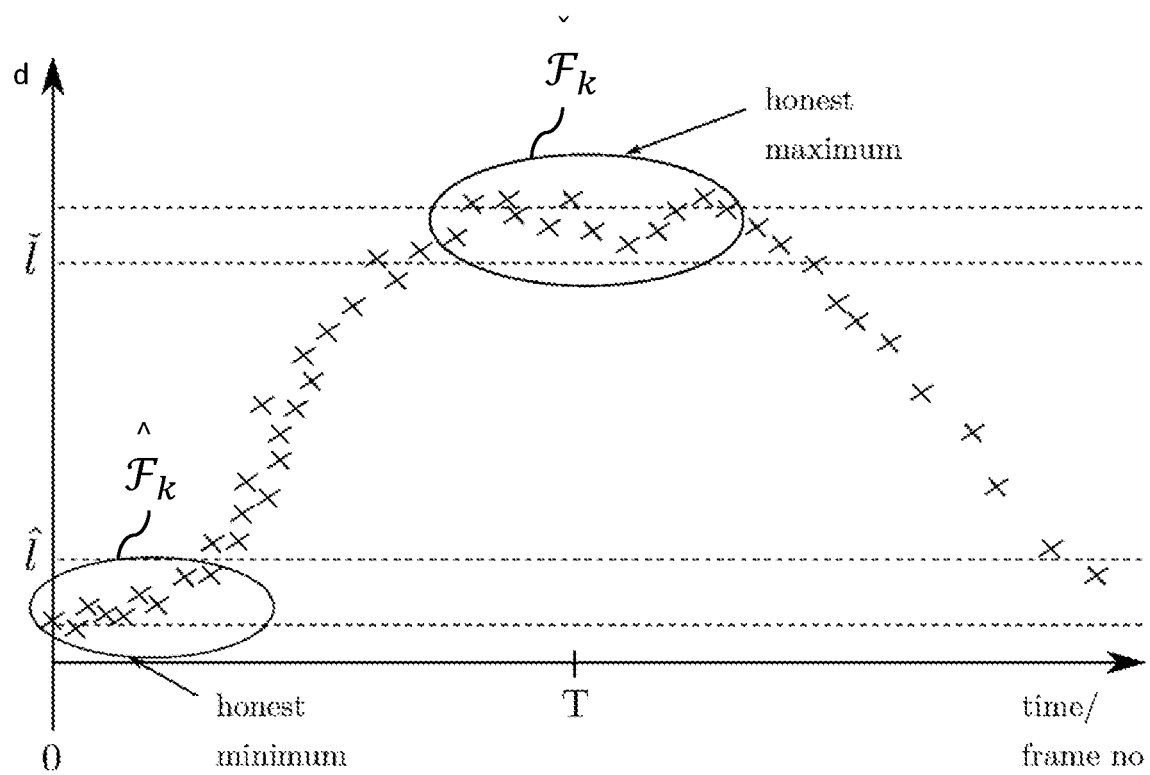
FIG. 7B illustrates honest extrema identification according to an embodiment.

However, in a real world walking scenario, there is typically a plurality of neighboring frames showing approximately the same distance of the individual's feet (e.g., during the period where both feet have contact with ground). Turning briefly to FIG. 7B, the figure illustrates the concept of honest extrema $\check{\mathcal{F}}_k, \hat{\mathcal{F}}_k$ in the human gait which can be used in accordance with an optional embodiment of the invention. The following assumptions are made: The human individual performs walk with a moderate variance of step lengths, e.g. on the order of half the average step length (½ sl, cf. FIG. 7A), or smaller, and a homogeneous gait pattern is performed without abrupt changes.

As it can be seen from FIG. 7B, around time T there are a number of frames in which the step length is close to its maximum value (as attained in the entire gait analysis). The "x" markers represent the distance d between the individual's feet in each respective frame over time. To identify the plurality of frames in relation to honest local extrema (i.e., honest local maxima $\check{\mathcal{F}}_k$/honest local minima $\hat{\mathcal{F}}_k$) with regards to the individual's foot distance, one can proceed as follows:

Fix $\hat{\alpha}, \check{\alpha} \in [0,1]$ such that $\hat{\alpha} < \check{\alpha}$, where $\hat{\alpha}$ and $\check{\alpha}$ are the percentiles of frames to be accepted as contributing to the computation of minimum and maximum step length, respectively.

Among all step lengths (obtained from the frames), let $\hat{l}$ denote the $\hat{\alpha}$ percentile, and $\check{l}$ denote the $\check{\alpha}$ percentile.

Let $\hat{\mathcal{F}} = \{f \in [F] : l(f) \leq \hat{l}\}$ $\check{\mathcal{F}} = \{f \in [F] : l(f) \geq \check{l}\}$ be the sets containing the honest minima frames and the honest maxima frames, respectively. Each of such sets includes a cluster $\check{\mathcal{F}}_k, \hat{\mathcal{F}}_k$ of frames associated with movements of the individual where the distance between the individual's feet goes through a local extremum. For example, inside such a cluster $\check{\mathcal{F}}_k$ associated with honest maxima frames the distances measured in the various frames of the cluster may fluctuate around a certain average value.

However, as explained earlier, the step length may still be determined from local maximum frames with sufficient accuracy. That is, within such cluster, multiple local maxima may exist. However, for determining the step length the whole cluster $\check{\mathcal{F}}_k$ provides meaningful information.

Further, the number of honest extrema clusters identified in a frame sequence gives a precise measure for counting the number of steps performed by the individual during the frame sequence. Actually, the number of honest maxima clusters directly corresponds to the number of steps performed by the individual. When counting all local maxima in the entire frame sequence it is to be expected that the derived number of local maximal significantly exceeds the number of steps performed by the individual because each cluster $\check{\mathcal{F}}_k$, typically includes multiple local maxima (or $\hat{\mathcal{F}}_k$ including multiple local minima). The sets can be uniquely decomposed into disjoint unions as follows:

$$\hat{\mathcal{F}} = \bigcup_{k=1}^{min} \hat{\mathcal{F}}_k, \check{\mathcal{F}} = \bigcup_{k=1}^{max} \check{\mathcal{F}}_k$$

such that for any k, $f \in \check{\mathcal{F}}_k$ and $g \in \check{\mathcal{F}}_k$ one has f<g; likewise, for any k, $f \in \hat{\mathcal{F}}_k$, and $g \in \hat{\mathcal{F}}_k$ one has f<g. Moreover, we require that for any k there is precisely one l (except possibly for k∈ {min,max}) such that either $$\hat{\mathcal{F}}_k < \check{\mathcal{F}}_l < \hat{\mathcal{F}}_{k+1}, \text{, or} \tag{i}$$

$$\check{\mathcal{F}}_k < \hat{\mathcal{F}}_l < \check{\mathcal{F}}_{k+1}. \tag{ii}$$

Here, A<B is defined as $V_{a \in A, b \in B}: a<b$.

Finding these two decompositions of $\check{\mathcal{F}}_l, \hat{\mathcal{F}}$ algorithmically is straightforward.

The $\hat{\mathcal{F}}_k$ are referred to as the honest minima frames, and $\check{\mathcal{F}}_k$ are referred to as the honest maxima frames. Then, min is the number of honest minima, and max is the number of honest maxima.

The value of the kth honest maximum/minimum can be chosen as some kind of average of the numbers in $\check{\mathcal{F}}_k/\hat{\mathcal{F}}_k$, e.g. one can take the mean value $$\frac{1}{\#\check{\mathcal{F}}_k} \sum_{x \in \check{\mathcal{F}}_k} x,$$

where #A denotes the cardinality of the set A.

The gait parameter determination module 130 of FIG. 1 computes 1210 a mean value sl of the distances sl* between the individual's foot locations in the determined local maximum frames flma* as the step length gait parameter. In the honest maxima embodiment, the system computes 1210 a mean value of the distance values derived from the honest maxima clusters $\check{\mathcal{F}}_k$.

In the simplified illustration of FIG. 7A all the sl* values have the same value. However, in a real world situation with a real video recording each distance sl* in a local maximum frame (or derived from an honest local maximum cluster) would very likely differ slightly from the distances in the previous and subsequent local maximum frames. That is, a mean value can be determined together with a standard deviation for the determined step length parameter. The gait parameter information is the gait parameter data 210 provided to a medically trained person 20. Thereby, a high standard deviation indicates to the medically trained person that the various step lengths of the individual show a significant deviation which can be considered when assessing the risk of fall for that individual. As mentioned earlier, the distance between the individual's foot locations may be measured directly in a respective frame based on the corresponding pixel coordinates, or it may be measured indirectly for a respective local maximum frame based on the distances of the individual's feet from the monocular camera device 201 using the pinhole projection model.

To determine a walking speed gait parameter of the individual, in the embodiment of FIG. 4B, the system can compute 1220 a walking distance of the individual based on the determined step length and the number of the local maximum frames identified in the video stream. The walking distance is then divided by the time interval associated with the sequence of frames associated with the walking distance to obtain 1230 the walking speed.

In an alternative implementation for obtaining 1210 the step length gait parameter, it is assumed that the camera 201 does not move during the recording of the video. The total distance traveled by the patient can then be computed 1220 as the sum: $D(1)+D(2)+\ldots+D(F-1)$, where $D(f)=|d(f+1)-d(f)|$, with $d(f)$ denoting the distance of the individual to the camera in frame f, and F is the number of frames in the video used for step length determination. The distance of the individual to the camera may be advantageously determined by applying the pinhole projection model, and using it to compute the distance to the individual's pelvis. However, other joint locations (e.g., the individual's head) may be used as well. In one implementation, an averaged joint location based on all joints or a particular subset of joint (e.g., head 318 (cf. FIG. 5) and pelvis 319 (cf. FIG. 5)) can be used as the reference point against which the distance to the camera is determined. In general, the distance can be determined for each frame as the distance between the camera and a reference point which is characteristic of the individual's current location.

Then, the total number of steps in the defined video stream sequence is determined for the tracked individual 10 as the number of "local maxima" in the step length sequence $sl(1), sl(2), \ldots, sl(F)$, where $sl(f)$ is the distance between the individuals feet in frame f. From these two gait parameters it is straightforward to compute the average step length, and the cadence.

Occasionally, the VNect implementation confuses joints that come in a left and a right variant (e.g., knees or feet where pairs of joints include a left and a right variant). To avoid this confusion, the following is proposed: Suppose jl and jr are the left and right variant of some joint. Then in each frame f the heat-map $H(f, jl)$ of joint jl is replaced by $H(f, jl)-H(f, jr)$, and accordingly for joint jr. The explanation for this replacement is as follows. Since $H(f, jr)$ encodes the likelihood for the right variant of joint j to be associated with a specific pixel in frame f, it is clear, that the higher the value of a particular point in $H(f, jr)$, the lower the likelihood that this particular point is associated with the left variant jl of the same joint j. Consequently, to prevent the algorithm for looking for jl in these positions, these likelihoods are subtracted from $H(f, jl)$.

Figure 8:
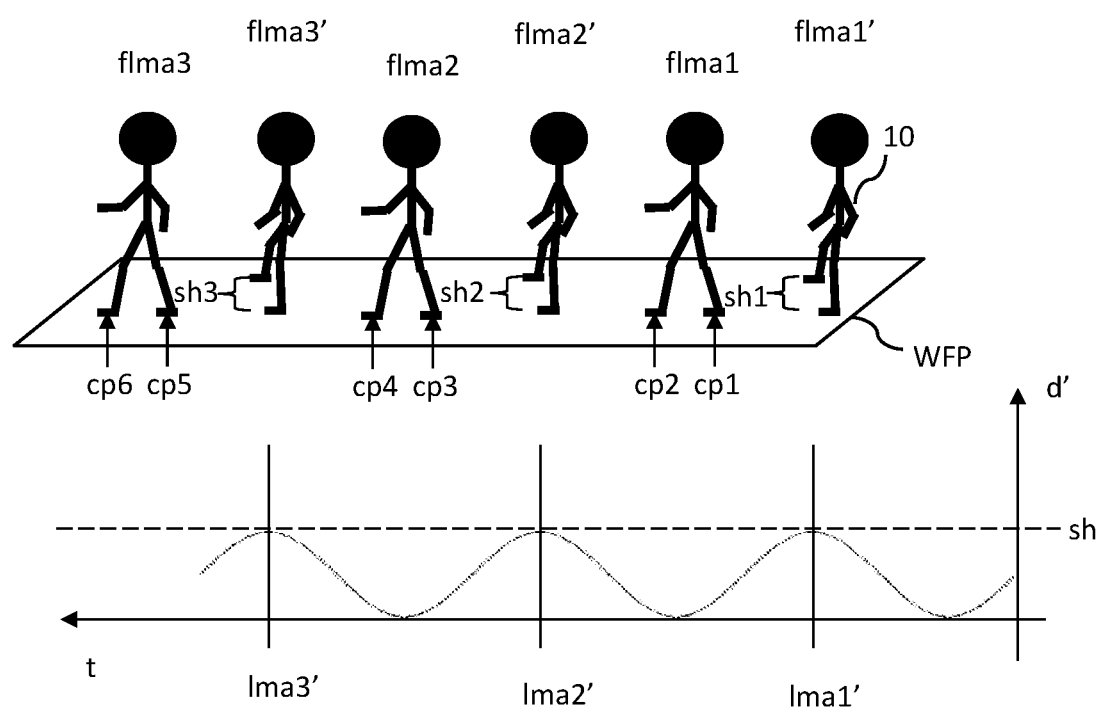
FIG. 8 illustrates step height gait parameter determination according to an embodiment.

FIG. 8 illustrates how a step height parameter of the individual 10 may be determined based on the information provided in the video stream in accordance with any one of the embodiments depicted in FIGS. 4C and 4D.

In the embodiment of FIG. 4C, the system extrapolates 1240 a walking floor plane (WFP) from floor contact points cp* of the individual's feet identified from the local maximum frames flma* which correspond to the frames also usable for step length determination. That is, the corresponding reference location is the location of the individual's second foot in the respective local maximum frame. Once the contact points cp* are determined the walking floor plane can be determined by a fitting plane through the contact points.

The system can then determine 1250 further local maximum frames flma*' with further local maxima lma*' of the distances d' of the individual's foot locations from the walking floor plane WFP. This second set of local maxima frames flma1', flma2', flma3' includes such frames where the distances sh1, sh2, sh3 between one foot of the individual and the WPF shows a local maximum. While walking, every second step the same foot passes such a local maximum. The local maxima lma1' and lma3' are associated with a first foot of the individual while the local maximum lma2' is associated with the second foot. Finally, the system computes 1260 a mean value sh of the further local maximum distances sh1, sh2, sh3 as the step height. As in FIG. 7A, the periodic behavior shown in the lower part of FIG. 8 is to be understood as a simplified schematic view. In a real-world scenario the step heights of each step would likely vary to some extent. Further, there may be a difference between the step height of the two feet of the individual based on anatomic properties of the individual. In such a case, it may be useful to provide a separate step height parameter for each foot to the medically trained person. Again, the standard deviation can provide valuable information regarding the smoothness of the individual's gait.

In the further embodiment of FIG. 4D, the step height gait parameter is determined by using the head or pelvis of the adjusted skeleton model in a respective local minimum frame as the corresponding reference location for the computation. In this embodiment, the system determines 1270 local minimum frames with local minima of the distances between the individual's foot locations and the corresponding reference location. In other words, in case the distance between one foot of the individual is at a local minimum with regards to a reference joint (head or pelvis) of the individual's body, the distance to the walking floor shows a local maximum. Once the local minimum frames are determined the system can compute 1280 a mean value of the distances between the individual's two feet in the local minimum frames as the step height. For example, the system may simply measure the distance between the two feet in each local minimum frame as one foot is touching the ground in the respective frame and the distances between the feet in local minimum frames are good approximations of the respective step heights. In an alternative embodiment, the person skilled in the art can apply the honest local extrema approach (disclosed in detail in the context of step length computation) also to the computation of the step height parameter.

Returning to FIG. 1, in one embodiment, the system 100 may further include a parameter scoring module 140. The scoring module 140 can associate one or more of the determined gait parameters with a score characterizing a risk of fall for the individual. The medically trained person 20 is familiar with such scoring schemes for assessing the risk of fall.

Figure 9:
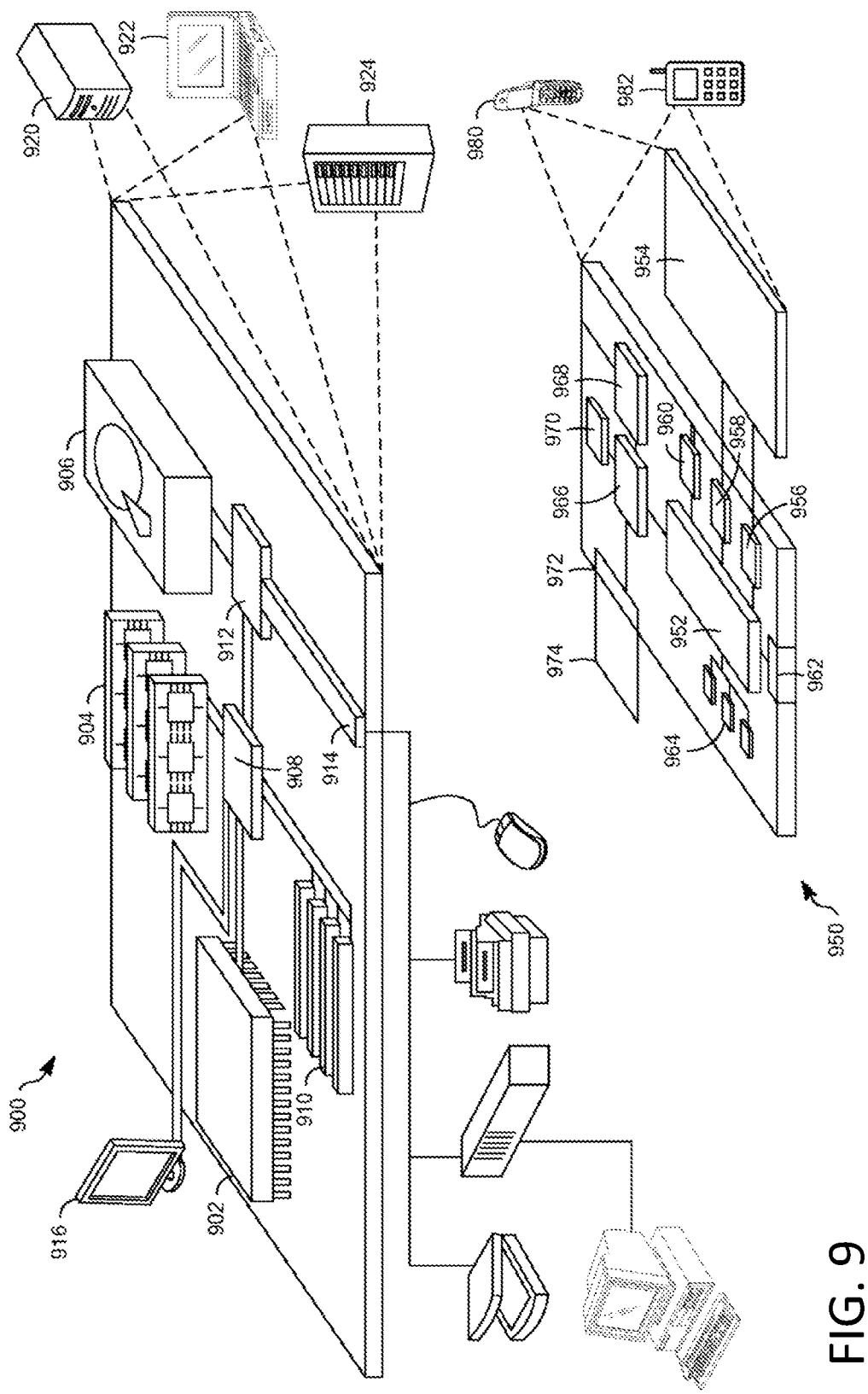
FIG. 9 is a diagram that shows an example of a generic computer device and a generic mobile computer device, which may be used with the techniques described herein.

FIG. 9 is a diagram that shows an example of a generic computer device 900 and a generic mobile computer device 950, which may be used with the techniques described here. Computing device 900 is intended to represent various forms of digital computers, such as laptops, desktops, workstations, personal digital assistants, servers, blade servers, mainframes, and other appropriate computers. Generic computer device may 900 correspond to the computer system 100 of FIG. 1. Computing device 950 is intended to represent various forms of mobile devices, such as personal digital assistants, cellular telephones, smart phones, and other similar computing devices. For example, computing device 950 may be a smartphone which includes a monocular RGB camera and can be used by the medically trained person to interact with the computer device 900. The components shown here, their connections and relationships, and their functions, are meant to be exemplary only, and are not meant to limit implementations of the inventions described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processing units and/or multiple buses may be used, as appropriate, along with multiple memories and types of memory. Also, multiple computing devices 900 may be connected, with each device providing portions of the necessary operations (e.g., as a server bank, a group of blade servers, or a processing device).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processing units. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952, that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method for human gait analysis based on a video stream obtained from a monocular camera device, the video stream including a plurality of frames reflecting a walk of a human individual, the method comprising:
    inferring, from the video stream, three-dimensional gait information, wherein the three-dimensional gait information includes estimates of joint locations of the individual including at least foot locations of the individual on each frame, the estimates being derived by matching, for each frame, two-dimensional joint coordinates of the respective frame with respective three-dimensional model information of a body of the individual, wherein the inferring further comprises:
        deriving heat-maps and location-maps for joint location estimation by using a convolutional neural network trained on three-dimensional human pose datasets, wherein a particular heat-map describes, for a corresponding frame, probability values that a particular joint is associated with respective pixels of the corresponding frame, and wherein a particular set of location-maps includes a plurality of location-maps, with each of the location-maps describing a distance of a particular joint to a root location for the corresponding frame in a respective spatial dimension;
        receiving a selection of at least a frame sequence of the video stream during which the joints of the human individual move over time;
        estimating a skeleton model of the individual by determining, for each frame of the selected sequence, a loss for each joint of a default skeleton model in each spatial coordinate, and adjusting the default skeleton model to compensate the determined losses to provide an adjusted skeleton model; and
        performing kinematic skeleton fitting per video frame using the adjusted skeleton model to determine a plurality of joint locations including at least the foot locations of feet of the individual on each frame; and determining one or more gait parameters of the individual based on the foot locations of the individual in local extrema frames showing local extrema of a distance between one foot location of the individual and a corresponding reference joint location, wherein at least one of the determined gait parameters is associated with a score characterizing a risk of fall for the individual.

2. The method of claim 1, wherein the deriving further comprises:
identifying a plurality of heat-map pixels in a particular heat-map wherein each of the identified pixels is associated with a same maximum probability value for the respective joint associated with the particular heat-map;
for each identified pixel, integrating heat-map values in a predefined area adjacent to the identified pixel; and
selecting the identified pixel with a highest integral value as the pixel associated with the respective joint location.

3. The method of claim 1, wherein the one or more gait parameters comprise a step length gait parameter, and wherein the corresponding reference joint location is the location of a second foot of the individual in a respective local maximum frame, the method further comprising:
computing a mean value of the distances between the individual's foot locations in determined local maximum frames as the step length gait parameter.

4. The method of claim 3, wherein the distance between the individual's foot locations is measured directly in a respective frame based on corresponding pixel coordinates.

5. The method of claim 3, wherein the distance between the individual's foot locations is measured indirectly for a respective local maximum frame based on the distances of feet of the individual from the monocular camera device.

6. The method of claim 3, wherein the one or more gait parameters further comprise a walking speed gait parameter, the method further comprising:
computing a walking distance of the individual based on the determined step length and a number of the local maximum frames identified in the video stream, and dividing the walking distance by a time interval associated with a sequence of frames associated with the walking distance to obtain the walking speed.

7. The method of claim 1, wherein the one or more gait parameters further comprise a step height gait parameter, the method further comprising:
extrapolating a walking floor plane from floor contact points of feet of the individual identified from local maximum frames wherein the corresponding reference joint location is the location of a second foot of the individual in the respective local maximum frame;
determining further local maximum frames with further local maxima of the distances of the individual's foot locations from the walking floor plane; and
computing a mean value of the further local maximum distances as the step height.

8. The method of claim 1, wherein the one or more gait parameters further comprise a step height gait parameter, and wherein the corresponding reference joint location is the location of a head or pelvis of the adjusted skeleton model in a respective local minimum frame, the method further comprising:
determining local minimum frames with local minima of the distances between the individual's foot locations and the corresponding reference joint location; and
computing a mean value of the distances between the individual's two feet in local minimum frames as the step height.

9. The method of claim 1, wherein, for determining the one or more gait parameters, clusters of honest local extrema frames are determined where the frames of a particular cluster contribute to computation of a step length of the individual in that an average distance value is computed based on all frames of the respective cluster so that the honest local extrema frames of the particular cluster include such frames which collectively reflect the distance between feet of the individual for a particular step of the individual.

10. A non-transitory computer program product for human gait analysis based on a video stream obtained from a monocular camera device, the video stream including a plurality of frames reflecting a walk of a human individual, the non-transitory computer program product comprising instructions that, when loaded into a memory of a computing device and executed by at least one processor of the computing device, cause the computing device to:
infer, from the video stream, three-dimensional gait information, wherein the three-dimensional gait information includes estimates of joint locations of the individual including at least foot locations of the individual on each frame, the estimates being derived by matching for each frame two-dimensional joint coordinates of the respective frame with respective three-dimensional model information of a body of the individual, wherein inferring the three-dimensional gait information includes:
deriving heat-maps and location-maps for joint location estimation by using a convolutional neural network trained on three-dimensional human pose datasets, wherein a particular heat-map describes, for a corresponding frame, probability values that a particular joint is associated with respective pixels of the corresponding frame, and wherein a particular set of location-maps includes a plurality of location-maps, with each of the location-maps describing a distance of a particular joint to a root location for the corresponding frame in a respective spatial dimension;
receiving a selection of at least a frame sequence of the video stream during which the joints of the human individual move over time;
estimating a skeleton model of the individual by determining, for each frame of the selected sequence, a loss for each joint of a default skeleton model in each spatial coordinate, and adjusting the default skeleton model to compensate the determined losses to provide an adjusted skeleton model; and
performing kinematic skeleton fitting per video frame using the adjusted skeleton model to determine a plurality of joint locations including at least the foot locations of feet of the individual on each frame; and
determine one or more gait parameters of the individual based on the individual's foot locations in local extrema frames showing local extrema of a distance between one foot location of the individual and a corresponding reference joint location, wherein at least one of the determined gait parameters is associated with a score characterizing a risk of fall for the individual.

11. The non-transitory computer program product of claim 10, wherein the one or more gait parameters comprise a step length gait parameter, and wherein the corresponding reference joint location is the location of a second foot of the individual in a respective local maximum frame, and wherein the instructions, when executed, further cause the computing device to:

compute a mean value of the distances between the individual's foot locations in determined local maximum frames as the step length gait parameter.

12. The non-transitory computer program product of claim 10, wherein the one or more gait parameters further comprise a step height gait parameter, wherein the instructions, when executed, further cause the computing device to:

extrapolate a walking floor plane from floor contact points of feet of the individual identified from local maximum frames wherein the corresponding reference joint location is the location of a second foot of the individual in the respective local maximum frame;

determine further local maximum frames with further local maxima of the distances of the individual's foot locations from the walking floor plane; and compute a mean value of the further local maximum distances as the step height.

13. A computer system for human gait analysis comprising:

an interface configured to obtain a video stream from a monocular camera device, the video stream comprising a plurality of frames reflecting a walk of a human individual; a skeletal motion extractor configured to extract from the video stream a skeletal motion associated with the individual, by inferring, from the obtained video stream, three-dimensional gait information, wherein the three-dimensional gait information includes estimates of joint locations of the individual including at least foot locations of the individual on each frame, the estimates being derived by matching for each frame two-dimensional joint coordinates of the respective frame with respective three-dimensional model information of a body of the individual, wherein inferring the three-dimensional gait information includes:

deriving heat-maps and location-maps for joint location estimation by using a convolutional neural network trained on three-dimensional human pose datasets, wherein a particular heat-map describes, for a corresponding frame, probability values that a particular joint is associated with respective pixels of the corresponding frame, and wherein a particular set of location-maps includes a plurality of location-maps, with each of the location-maps describing a distance of a particular joint to a root location for the corresponding frame in a respective spatial dimension;

receiving a selection of at least a frame sequence of the video stream during which the joints of the human individual move over time;

estimating a skeleton model of the individual by determining, for each frame of the selected sequence, a loss for each joint of a default skeleton model in each spatial coordinate, and adjusting the default skeleton model to compensate the determined losses to provide an adjusted skeleton model; and performing kinematic skeleton fitting per video frame using the adjusted skeleton model to determine a plurality of joint locations including at least the foot locations of feet of the individual on each frame;

a gait parameter determining module configured to determine one or more gait parameters of the individual based on the individual's foot locations in local extrema frames showing local extrema of a distance between one foot location of the individual and a corresponding reference joint location; and a scoring module configured to associate one or more of the determined gait parameters with a score characterizing a risk of fall for the individual.

14. The system of claim 13, wherein the extractor module further comprises:

a two-dimensional joint coordinate estimator module configured to provide, for each frame, estimates of two-dimensional joint coordinates of each joint, together with a confidence value for each joint; and a three-dimensional fitting module configured to fit a three-dimensional human body model to the two-dimensional joint coordinates.

15. The system of claim 13, wherein the one or more gait parameters comprise a step length gait parameter, and wherein the corresponding reference joint location is the location of a second foot of the individual in a respective local maximum frame, the gait parameter determining module further configured to:

compute a total distance traveled by the individual by applying a pinhole projection model to determine distances between the camera and a reference point being characteristic of a current location of the individual for at least a first and a second frame, the first and second frame defining a video stream sequence to be used for step length analysis, the traveled distance derived from the determined distances;

determining a number of steps in the defined video stream sequence as the number of local maximum frames with local maxima of the distance between feet of the individual; and dividing the computed traveled distance by the number of local maximum frames to obtain an average step length.

16. The system of claim 13, wherein the one or more gait parameters further comprise a step height gait parameter, the gait parameter determining module further configured:

to determine local minimum frames with local minima of the distances between the individual's foot locations and a head or pelvis of the adjusted skeleton model; and to compute a mean value of the distances between two feet of the individual in local minimum frames as the step height.

17. The system of claim 13, wherein the gait parameter determining module is further configured to determine clusters of honest local extrema frames where the frames of a particular cluster contribute to the computation of a step length of the individual in that an average distance value is computed based on all frames of the respective cluster so that the honest local extrema frames of the particular cluster include such frames which collectively reflect the distance between feet of the individual for a particular step of the individual.

* * * * *